US006468416B1

(12) United States Patent
Nakamura et al.

(10) Patent No.: US 6,468,416 B1
(45) Date of Patent: Oct. 22, 2002

(54) METHOD FOR ASSAYING L-PHENYLALANINE AND L-PHENYLALANINE SENSOR

(75) Inventors: Kenji Nakamura; Toru Yokoyama; Naoki Shinozuka, all of Hokkaido (JP)

(73) Assignee: Sapporo Immuno Diagnostic Laboratory, Hokkaido (JP)

( * ) Notice: Subject to any disclaimer, the term of this patent is extended or adjusted under 35 U.S.C. 154(b) by 0 days.

(21) Appl. No.: 09/743,571
(22) PCT Filed: Jul. 16, 1998
(86) PCT No.: PCT/JP98/03194
§ 371 (c)(1), (2), (4) Date: Jan. 12, 2001
(87) PCT Pub. No.: WO00/04378
PCT Pub. Date: Jan. 27, 2000

(51) Int. Cl.[7] .............................................. G01N 27/327
(52) U.S. Cl. ............................ 205/777.5; 204/403.14; 204/403.1; 204/403.06
(58) Field of Search ........................ 204/403, 403.06, 204/403.1, 403.14; 205/777.5

(56) References Cited

U.S. PATENT DOCUMENTS

| | | | |
|---|---|---|---|
| 4,897,173 A | 1/1990 | Nankai et al. ............... 204/403 |
| 5,304,468 A | 4/1994 | Phillips et al. ................ 435/14 |
| 5,360,595 A | 11/1994 | Bell et al. ..................... 422/56 |
| 5,520,786 A | 5/1996 | Bloczynaski et al. ....... 204/403 |
| 5,639,672 A | 6/1997 | Burd et al. ................... 436/525 |
| 5,658,443 A | * 8/1997 | Yamamoto et al. ......... 204/403 |
| 5,672,256 A | * 9/1997 | Yee ............................. 204/403 |

FOREIGN PATENT DOCUMENTS

| | | |
|---|---|---|
| EP | 0351891 B1 | 1/1990 |
| JP | 63-129996 | 6/1988 |

OTHER PUBLICATIONS

Hayashi et al., " . . . Amino acids in plasma samples . . . ", J. Chromatography 274, 318–324 (1993) Month Unknown.
Guthrie et al., "A simple phenylalanine method for detecting . . . ", Pediatrics 32, 338–343 (1963) Month Unknown.
Bergmeyer ed., "L–Phenylalanine and L–Tyrosine", Methods of Enzymatic Analysis 8, 405–411 (1985) Month Unknown.
Hirokazu Koyama, "A simple and rapid enzymatic determination of L–Phenylalanine . . . ", Clinica Chimica Acta 136, 131–136 (1984) Month Unknown.
Huang et al., "Determination of L–Phenylalanine Based on an NADH–Detecting . . . ", Analytical Chemistry 70, 5 991–997 (1998) March.
Ihn et al., "Preparation and comparison of Proteus vulgaris and Proteus . . . ", Bioelectrochemistry and BioEnergetics 21, 223–231 (1989) Month Unknown.

(List continued on next page.)

Primary Examiner—T. Tung
Assistant Examiner—Alexander Noguerola
(74) Attorney, Agent, or Firm—Nixon & Vanderhye P.C.

(57) ABSTRACT

An L-phenylalanine sensor wherein all of the reagents required in determining L-phenylalanine are integrated together, thereby enabling quick and convenient quantification without resort to any special equipment, devices or techniques. This sensor is fabricated by integrating L-phenylalanine dehydrogenase, oxidized nicotinamide adenine dinucleotide (NAD$^+$) or oxidized nicotinamide adenine dinucleotide phosphate (NADP$^+$) as a coenzyme and an electron mediator, which are employed as reagents, with an electrode system comprising at least a working electrode and a counter electrode. Also, a method of determining L-phenylalanine which comprises adding a sample containing L-phenylalanine to the above-described sensor and electrochemically quantitating L-phenylalanine is provided.

3 Claims, 8 Drawing Sheets

OTHER PUBLICATIONS

Hummel et al., "Enzymatic Determination of L–Phenylalanine and Phenylpyruvate . . .", Analytical Biochemistry 170, 397–401 (1988) Month Unknown.

Wendel et al., "Monitoring of Phenylketonuria: A Colorimetric . . .", Analytical Biochemistry 180, 91–94(1988) Month Unknown.

Wendel et al., "A new approach to the newborn . . .", Clinica Chimica Acta 192, 165–170 (1990) Month Unknown.

Wendel et al., "Towards self–monitoring . . .", Eur. J. Pediatrics 155 (Suppl.. 1), S105–S107 (1996) Month Unknown.

Naruse et al., "A method of PKU screening using phenylalanine . . .", Screening 1, 63–66 (1992).

Ishiyama et al., "Novel Disulfonated Tetrazolium . . .", Analyst 120, 113–116 (1995) Jan.

* cited by examiner

METHOD FOR ASSAYING L-PHENYLALANINE AND L-PHENYLALANINE SENSOR

FIELD OF THE INVENTION

This invention relates to a biosensor by which the concentration of L-phenylalanine contained in various samples can be quickly and conveniently quantitated without resort to any troublesome pretreatments. More particularly speaking, it relates to a biosensor which is useful in quantitating L-phenylalanine contained in biological samples (blood, urine, saliva, sweat, etc.), food samples and the like by an electrochemical measurement method with the use of L-phenylalanine dehydrogenase, etc. This method is particularly significant in newborn mass screening for detecting phenylketonuria (PKU), which is an amino acid metabolic error, at the early stage, or monitoring the daily living of patients suffering form this disease.

BACKGROUND OF THE INVENTION

L-Phenylalanine is an important amino acid which is one of the essential amino acids and contained in a large amount of biological samples as well as in foods and drinks employed as L-phenylalanine sources. On the other hand, the disease known as PKU is one of typical hereditary amino acid metabolic errors wherein tyrosine is not synthesized due to L-phenylalanine dehydrogenase deficiency and thus L-phenylalanine is pooled at an abnormally high level in the blood. When allowed to stand, PKU induces serious intellectual disturbance, speech disturbance, amelanotic symptom, etc.

To prevent this disease, newborn mass screening has been widely carried out in Japan and foreign countries. As a typical example of methods for determining L-phenylalanine concentration in the blood, the Guthrie method with the use of dried blood spot has been employed and has largely contributed to early diagnoses.

Patients with PKU thus found should have a diet therapy restricting their L-phenylalanine intake. Namely, such patients should have specially prepared dishes with the elimination or reduction of L-phenylalanine at least until reaching the majority, preferably throughout their lives. Since L-phenylalanine is one of the essential amino acids for the human-body, the L-phenylalanine concentration should be strictly regulated so that it can be taken at the maximum level without inducing brain disturbance, etc. but yet at the minimum level required for the growth of the body. In treating PKU, it is therefore essential to monitor not only the phenylalanine level in the blood but also the phenylalanine intake in the daily diet.

Under these circumstances, examples of methods for determining L-phenylalanine by using blood as samples include the liquid chromatographic method (Journal of Chromatography, Vol. 274, p. 318 (1983)) and the bioassay method with the use of dried blood spot, i.e., the method widely known as the Guthrie method (Pediatrics, Vol. 32, p. 338 (1963)). In the former method it is necessary to subject samples to a specific pretreatment and to use expensive measuring instruments. Although the latter method can be conveniently carried out, it takes a long time to complete the reaction and the results need to be scrutinized with the naked eye. Namely, each of these methods suffers from some problems from the viewpoint of convenience or rapidness in quantification.

There have been also reported determination methods with the use of enzymes, for example, a method with the use of L-phenylalanine ammonia-lyase (Methods of Enzymatic Analysis, Vol. 8, p. 405 (1985)), a method with the use of L-phenylalanine oxidase (Clinica Chimica Acta, Vol. 136, p. 131 (1984)) and a method with the use of L-phenylalanine dehydrogenase (Japanese Laid-Open Patent Publication No. 63-129996(A)). In these documents, the usefulness of these methods in quantification is pointed out. In particular, the method of determining phenylalanine in the blood with the use of L-,phenylalanine dehydrogenase is reported in detail by Hummel et al. (Analytical Biochemistry, Vol. 170, p. 397 (1988)) and Wendel et al. (Analytical Biochemistry, Vol. 180, p. 91 (1989), Clinica Chimica Acta, Vol. 192, p. 165 (1990)). In each of these methods, the blood employed as a,sample is subjected to various pretreatments and then an enzyme reaction is carried out. In addition, the quantification cannot be performed unless expensive and relatively large-scale measuring instruments (a spectrophotometer, etc.) are employed.

In recent years, biosensors, in particular, sensors with the use of enzymes have been vigorously developed. Through them all, it has become possible to conveniently and highly accurately determine blood glucose level as disclosed in EP 351891 and WO 86/07632. Although attempts have been recently made by Huang et al. to determine L-phenylalanine (Analytical Chemistry, Vol. 70, p. 991 (1998)), there still remain a number of problems to be solved in putting the sensor to practical use.

In this method, a carbon paste containing L-phenylalanine dehydrogenase mixed with two other enzymes (i.e., salicylate hydroxylase and tyrosinase) is filled in a tube (1.2 mm×1.5 mm×30 mm) which is provided with a copper wire as a lead wire. After polishing the electrode surface, it is employed as a working electrode. A detection unit composed of this working electrode, a reference electrode made of silver/silver chloride (Ag/AgCl) and a counter electrode made of platinum is connected to a reactor to thereby fabricate a determination unit. The determination is carried out by mixing a buffer, a salicylic acid solution and oxidized nicotinamide adenine dinucleotide (NAD$^+$) in the reactor, adding a sample, and calculating the L-phenylalanine concentration by using a computer from the response current obtained after the reaction. Thus phenylalanine in a concentration range of from 20 to 150 $\mu$M can be quantitated and the detection sensitivity is 5 $\mu$M. However, there still remain problems to be solved in, for example, the stability of the response and the storage stability of the enzyme electrode thus constructed.

Although the biosensor technology as described above is just making it possible to determine L-phenylalanine by using L-phenylalanine dehydrogenase, a quick and convenient quantification is still impossible since it is necessary in this method to prepare reagents and instruments and perform troublesome procedures and operations. Although it is desirable for patients with PKU that L-phenylalanine can be conveniently determined at home so as to monitor the blood L-phenylalanine level and examine foods and drinks to be cooked, it is still difficult at the present stage.

Under these circumstances, it is an object of the present invention to provide a biosensor, by which L-phenylalanine can be highly accurately, quickly and conveniently quantitated without resort to the use of many reagents, large-scaled measuring devices or instruments, troublesome pretreatments or special techniques, and a determination method therefor.

SUMMARY OF THE INVENTION

To achieve the above-described object, the present invention provides an L-phenylalanine sensor composed of an electrode system, which comprises at least a working electrode and a counter electrode formed on an insulating support, and a reagent reaction layer, which contains as reaction reagents at least L-phenylalanine dehydrogenase, NAD$^+$ or oxidized nicotinamide adenine dinucleotide phosphate (NADP$^+$) as a coenzyme and an electron mediator and is integrated with the above electrode system, and a method of determining L-phenylalanine by which L-phenylalanine. can be electrochemically quantitated simply by adding a sample to the above-described sensor without resort to any troublesome pretreatments.

In the L-phenylalanine sensor according to the present invention, an absorbent carrier containing as reaction reagents at least L-phenylalanine dehydrogenase, NAD$^+$ or NADP$^+$ and an electron mediator is located as a reagent reaction layer between the electrodes of an electrode system, which comprises at least a working electrode and a counter electrode provided opposite to each other on an insulating support, and integrated with the electrode system. Owing to this structure, both of the enzyme reaction and the electrode reaction between the electron mediator and the electrode surface can be carried out and, furthermore, the sensor can be downsized. Use of the absorbent carrier also makes it possible to add a sample smoothly in a definite amount.

The biosensor according to the present invention having the structure as described above makes it possible to conveniently and highly accurately quantitate L-phenylalanine contained in a sample without using any expensive special instruments or adding reagents such as an enzyme to the sample.

DESCRIPTION OF THE INVENTION

According to the present invention, a sample is added to an L-phenylalanine sensor wherein an electrode and a reagent reaction layer are integrated together. Thus, the L-phenylalanine contained in the sample is introduced into the enzyme reaction by the L-phenylalanine dehydrogenase and NAD$^+$ or NADP$^+$. As a result, phenylpyruvate is formed and NAD(P)$^+$ is reduced into NAD(P)H. In association therewith, the electron mediator is reduced due to the electron transfer from NAD(P)H. Subsequently, a potential is applied and thus the reduced electron mediator is oxidized as the electrode reaction, thereby causing the generation of an oxidation current. Thus, L-phenylalanine can be electrochemically quantitated with the guidance of the response current corresponding to the substrate concentration.

The present invention further provides an L-phenylalanine sensor composed of an electrode system, which comprises at least a working electrode and a counter electrode formed on an insulating support, and a reagent reaction layer which contains reaction reagents and is integrated with the above-described electrode system. In this L-phenylalanine sensor, the reagent reaction layer comprises an,absorbent carrier containing at least L-phenylalanine dehydrogenase, NAD$^+$ or NADP$^+$ and an electron mediator and is located in a part where the electrode reaction between these electrode arises, thereby giving an integral structure.

Use of the absorbent carrier in the reagent reaction layer makes it possible to provide a method of conveniently maintaining the reaction reagents while achieving excellent storage stability of the reagents and excellent response stability with neither processing the electrode system nor affecting (for example, worsening the performance) the same. Moreover, a definite amount of a sample can be quickly introduced into the reagent reaction layer thereby. Thus, L-phenylalanine can be highly accurately and conveniently quantitated within a short period of time.

Figure 1:
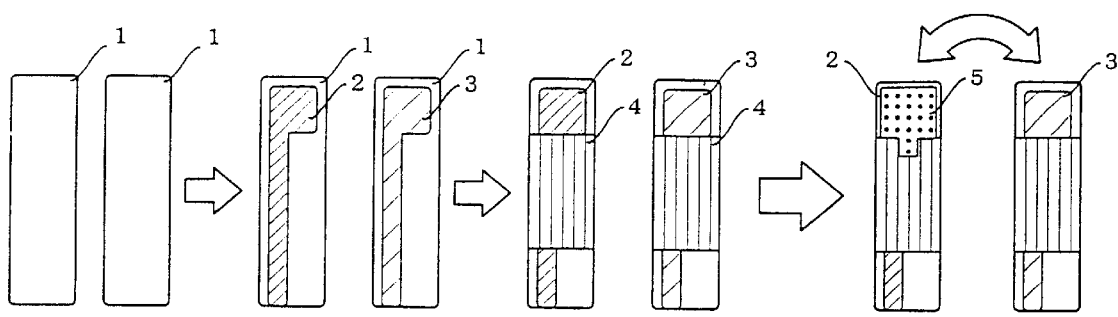
FIG. 1 is a diagrammatic illustration of the components of an embodiment of the L-phenylalanine sensor according to the present invention.
Figure 1:
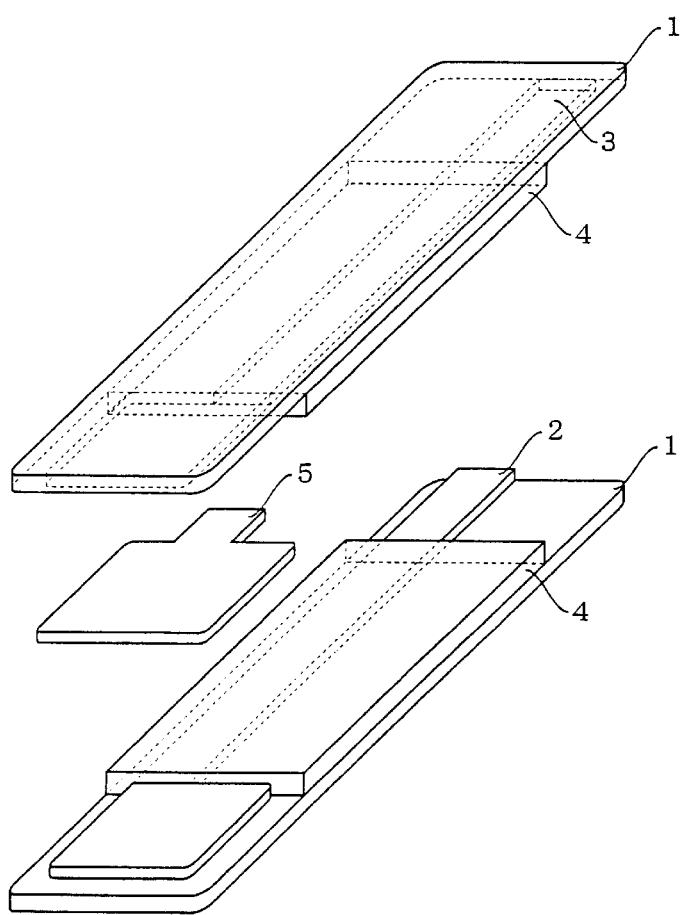

In these drawings, each symbol has the following meaning:

1: insulating support; 2: working electrode; 3: counter electrode; 4: insulating layer; 5: absorbent carrier; 11: sample; 12: L-phenylalanine sensor; 13: portable meter for L-phenylalanine sensor; 14: switch; 15: timer; 16: potential applier; 17: detector; 18: central processing unit; and 19: display.

BEST MODE FOR CARRYING OUT THE INVENTION

The electrode system to be used in the present invention may be made of an arbitrary conductive material without particular restriction. As the material, use can be made of iridium, osmium, carbon, gold, silver, silver/silver chloride, iron, copper, nickel, platinum, platinum black, palladium, lutenium, rhodium, etc. and alloys of these metals. As the result of examining various materials, it is known that carbon materials are favorable as the working electrode in the electrode system of the L-phenylalanine sensor according to the present invention, since they are less expensive and chemically stable.

The term "carbon materials" as used herein generally means materials containing carbon. The carbon materials usable herein are not restricted. Namely, those commonly employed in the so-called carbon electrodes may be employed therefor. For example, use can be made of carbon fiber, carbon black, carbon paste, glassy carbon, graphite and the like.

By using such a carbon material, electrodes are formed on the insulating support by a conventional method. Generally, the carbon material is processed into a paste with the use of a resin binder, etc. Then the paste is subjected to screen printing and dried by heating thereby forming the electrodes. It is also possible that a lead wire for connecting the electrode part to the determination unit is provided by the screen printing in such a manner that a silver lead part comes into contact with the carbon electrode part.

Examples of the insulating support include glass, glass epoxy, ceramics, plastics and the like. An arbitrary material may be used therefor without particular restriction, so long as it is not deteriorated in the step of the printing for forming the electrode part or in the step of the addition of a sample. For example, plastic films made of polyester, polyethylene, polyethylene terephthalate, polystyrene, polypropylene, etc. are inexpensive. By further taking the adhesiveness to a conductive ink and processability into consideration, it has been found out that a polyester film is favorable herein.

The printing method is not restricted to the screen printing but other methods (gravure printing, offset printing, inkjet printing, etc.) may also be applied thereto.

The L-phenylalanine dehydrogenase to be used in the present invention may be an arbitrary one, so long as it is accompanied by $NAD^+$ or $NADP^+$ as a coenzyme. Namely, enzymes with various origins and those obtained therefrom by gene recombination techniques may be used therefor. Examples thereof include enzymes produced by bacteria belonging to the genus Actinomcyes, microorganisms belonging to the genus Sporosarcina, bacteria belonging to the genus Bacillus, bacteria belonging to the genus Brevibacterium and bacteria belonging to the genus Rhodococcus. Among all, L-phenylalanine dehydrogenase originating in *Thermoactinomyces intermedius* is little affected in the drying step for forming the reagent reaction layer owing to its thermophilic nature and is excellent in the substrate specificity and reactivity. Thus, it is preferable as the enzyme constituting the L-phenylalanine sensor in the present invention.

The electron mediator to be used in the present invention is not particularly restricted, so long as it is a substance which is electrochemically reduced by NADH or NADPH formed by the enzyme reaction and oxidized at the electrode. For example, use can be made therefor of quiones, cytochromes, viologens, phenazines, phenoxazines, phenothiazines, ferricyanides, ferredoxins, ferrocene and derivatives thereof. Among all, phenazines are excellent in response stability. In particular, it has been found out that 1-methoxy-5-methylphenadinium methyl sulfate (1-methoxy PMS) is favorable as the electron mediator in the present invention, since it is excellent in the storage stability in the reagent reaction layer and the response stability in the electrode reaction.

The term "reagent reaction layer" as used herein means a layer which is in contact with the electrode system and sustains the reaction reagents and in which the reagents react with L-phenylalanine in a sample. It contains at least L-phenylalanine dehydrogenase, $NAD^+$ or $NADP^+$ and an electron mediator. As the results of the enzyme reaction and the electrode reaction between the electron mediator and the electrode surface, the response current can be electrochemically measured in this layer. To form this reagent reaction layer, various methods commonly used in the art may be employed.

For example, a reagent solution is dropped onto the electrodes and then dried. Alternatively, a reagent solution is absorbed by a porous material (a nylon nonwoven fabric, etc.), dried and then put on the electrodes. After examining various methods, it turned out to be preferable in the determination according to the present invention that the reagent reaction layer has a structure formed by providing an absorbent carrier, which is obtained by using a polymer material, etc., dropping individual reagents or a mixture thereof thereon and drying, or immersing a polymer material, etc. in a reagent solution and drying, in a part where the electrode reaction between at least the working electrode and the counter electrode in the electrode system occurs.

By using the reagent reaction layer comprising the absorbent carrier, a definite amount of a sample can be rapidly added without resort to the use of any special instruments in the step of adding the sample owing to the absorptivity of the absorbent carrier. Moreover, the L-phenylalanine sensor can be conveniently fabricated thereby without directly processing the electrode reaction part.

The absorbent carrier may be made of an arbitrary material, so long as it has a hydrophilic nature and can absorb a solution. For example, use can be made therefor of fibers (glass fiber, silica fiber, cellulose fiber, etc.), carboxymethylcellulose, diethylaminoethylcellulose, cellulose acetate, cellulose-mixed ester, nylon nonwoven fabric, nitrocellulose, polyether sulfone, polyester nonwoven fabric, polytetrafluoroethylene (PTFE), polypropylene, etc. Among all, it is known that cellulose fiber is favorable as the absorbent carrier in the L-phenylalanine sensor according to the present invention. This is because when an enzyme, $NAD^+$ or $NADP^+$ and an electron mediator are added to cellulose fiber, these substances can remain stable without suffering from any deterioration in function and are not undesirably affected in the step of the detection, thereby ensuring highly accurate quantification.

EXAMPLES

Now, the present invention will be illustrated in greater detail by referring the following Examples. However, it is to be understood that the invention is not construed as being limited thereto.

Example 1

Fabrication of Electrodes and Absorbent Carrier

FIG. 1 is a diagrammatic illustration of the components of an embodiment of the L-phenylalanine sensor according to the present invention.

On an insulating support 1 made of a polyester film (manufactured by Diafoil Hoechst), a working electrode 2 and a counter electrode 3 were formed by the screen printing method respectively with the use of a conductive graphite ink (manufactured by Acheson) and a conductive silver/silver chloride ink (manufactured by Acheson) and dried by heating (60° C., 1 hour). Subsequently, an insulating layer 4 was formed at a part of each electrode by the screen printing method with the use of a insulating ink (manufactured by Acheson) and dried by heating (60° C., 1 hour), thereby forming an electrode system by the printing method.

L-Phenylalanine dehydrogenase (PheDH: EC 1.4.1.20, manufactured by Unitika), $NAD^+$ (manufactured by Oriental Yeast) employed as a coenzyme and 1-methoxy PMS (manufactured by Dojin Kagaku Kenkyusho) employed as an electron mediator were dissolved in a borate buffer (pH 8.0, 20 mM) to give a mixed reaction reagent solution which was then absorbed by an absorbent carrier 5 made of a cellulose fiber (manufactured by Advantec Toyo) and dried by heating (40° C., 15 minutes). Thus, an absorbent carrier 5 containing the reaction reagents was obtained.

The absorbent carrier 5 containing the reaction reagents was provided as a reaction layer in the electrode reaction part of the electrode system comprising the working electrode 2 and the counter electrode 3 located opposite to each other, thereby fabricating an L-phenylalanine sensor.

Example 2

Figure 2:
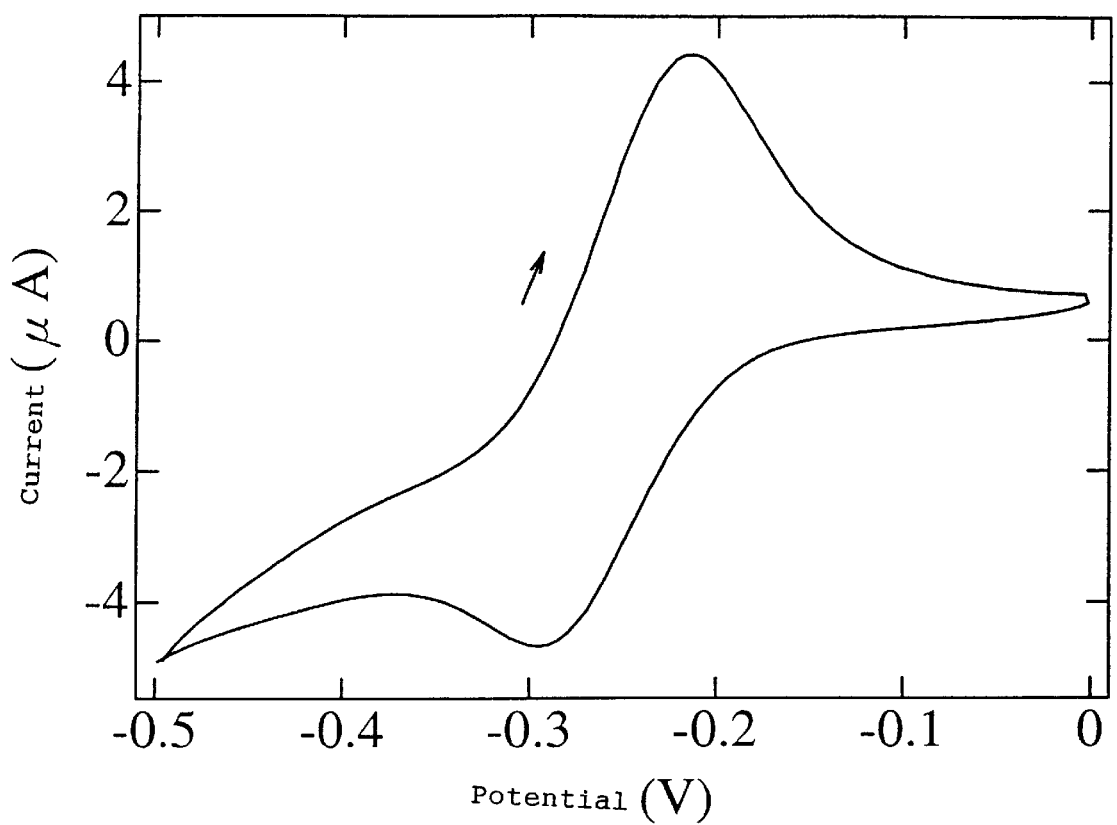
FIG. 2 is a graph which shows the response data to the electron mediator in Example 2.

Determination of Electrode Reaction Concerning the determination of the electrode reaction, FIG. 2 shows the oxidation-reduction response data to 1-methoxy PMS employed as the electron-mediator.

In this Example, the L-phenylalanine sensor fabricated in Example 1 was used and 5 μl of an L-phenylalanine-free buffer (pH 10.5, 0.2 M glycine-KCl-KOH) was added to the end face of the absorbent carrier 5 in the sensor. Namely, no enzyme reaction arose since the sample contained no substrate (i.e., L-phenylalanine). Therefore, these data show the cyclic voltammogram (sweep rate: 20 mV/sec, Model HZ-3000 manufactured by Hokuto Denko) of 1-methoxy PMS.

In this case, the final concentrations of the reaction reagents in each determination were adjusted as follows: PheDH,: 1 U; NAD$^+$: 5 mM; and 1-methoxy PMS: 0.5 mM.

The peak potential appeared at around −220 mV in the oxidation side and at around −300 mV in the reduction side. Thus a good oxidation reduction response was observed without suffering from any undesirably effects such as disturbance by the absorbent carrier or the reaction reagents contained therein.

Example 3
Quantification of L-phenylalanine (Standard Solutions)

Figure 3:
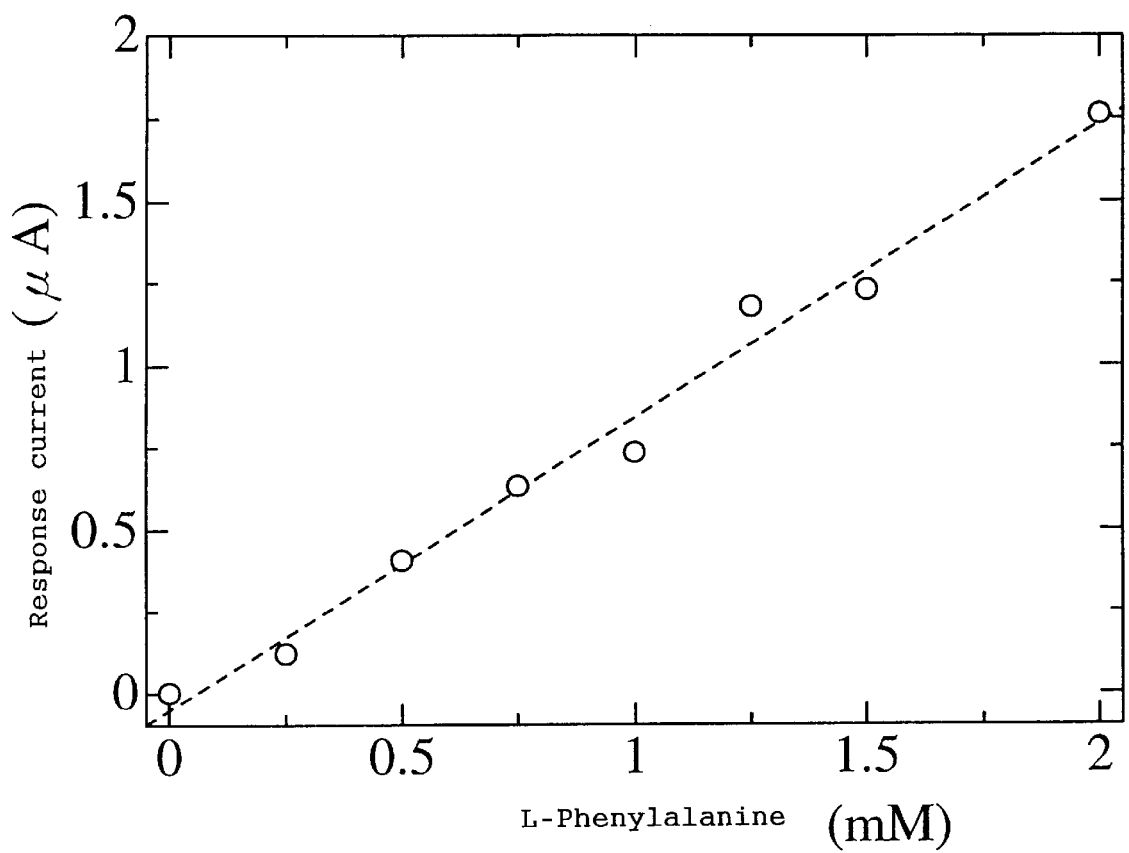
FIG. 3 is a graph which shows the response data to L-phenylalanine (standard solutions) in Example 3.

By using standard solutions containing L-phenylalanine as samples, determination was carried out with the L-phenylalanine sensor fabricated in Example 1. FIG. 3 shows the results.

5 μl of each sample was added. After 60 seconds, a potential of −220 mV vs. Ag/AgCl (i.e., counter electrode) was applied and the response current was measured (Model HZ-3000 manufactured by Hokuto Denko).

In this case, the final concentrations of the reaction reagents in each determination were adjusted as follows: L-phenylalanine dehydrogenase: 1 U; NAD$^+$: 5 mM; and 1-methoxy PMS: 0.5 mM.

Figure 4:
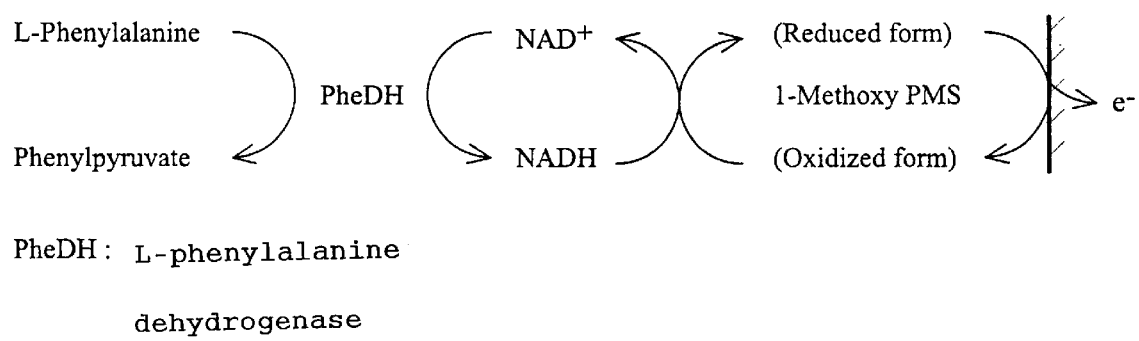
FIG. 4 is a reaction model of the determination of L-phenylalanine.

When the sample was added to the absorbent carrier 5 serving as the reagent reaction layer, L-phenylalanine in the sample underwent the enzyme reaction with the L-phenylalanine dehydrogenase and NAD$^+$ so that phenylpyruvate was formed. Thus NAD$^+$ was reduced to NADH and, in turn, 1-methoxy PMS was reduced due to the electron transfer. Subsequently, an oxidation current of reduced 1-methoxy PMS was obtained by the electrode reaction due to the application of the potential as described above. This current level depended on the concentration of L-phenylalanine which was the substrate. FIG. 4 illustrates this reaction model of the L-phenylalanine determination according to the present invention.

Thus, highly favorable linear data were obtained within an L-phenylalanine concentration range of from 0 to 2 mM.

Example 4
Quantification of L-phenylalanine (Blood Samples)

Figure 5:
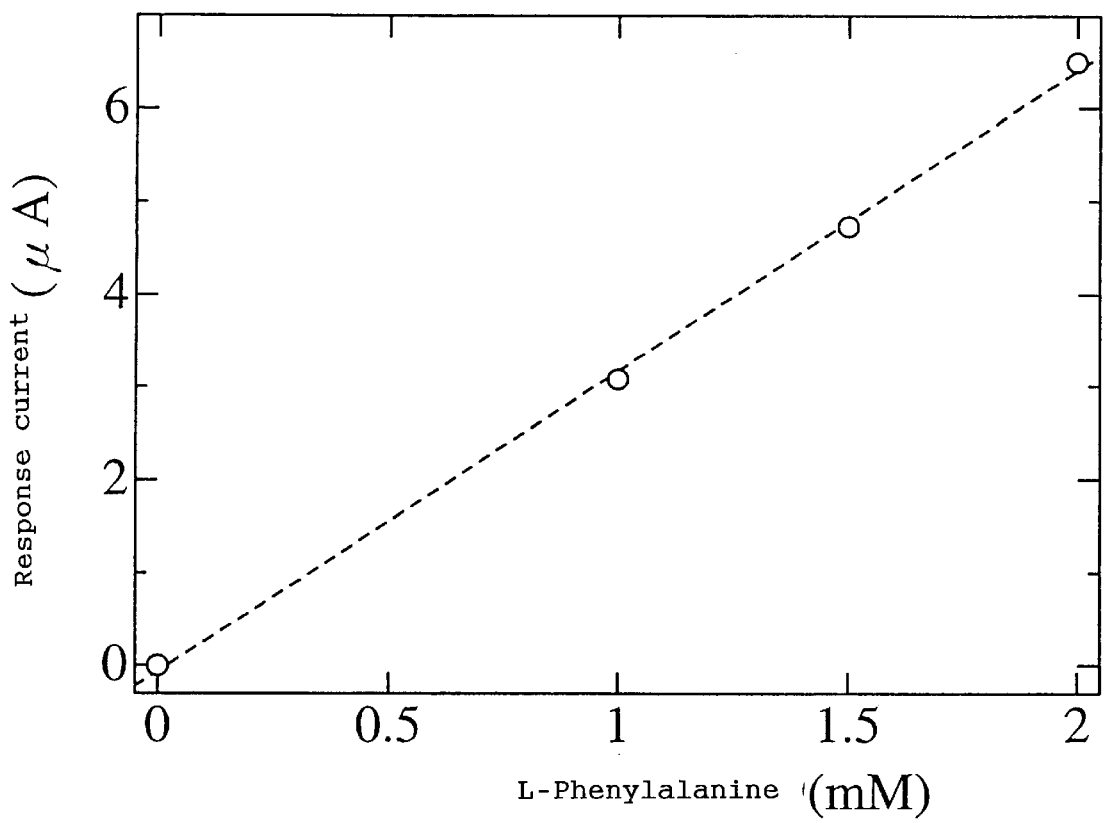
FIG. 5 is a graph which shows the response data to L-phenylalanine (blood samples) in Example 4.

By referring to Example 3, L-phenylalanine was determined by using L-phenylalanine-containing blood samples. FIG. 5 shows the results.

7.5 μl of each sample was added to the insulating support 5 of the sensor. After 120 seconds, a potential of −180 mV vs. Ag/AgCl (i.e., counter electrode) was applied and the response current was measured.

In this case, the final concentrations of the reaction reagents in each determination were adjusted as follows: L-phenylalanine dehydrogenase: 2 U; NAD$^+$: 5 mM: and 1-methoxy PMS: 0.5 mM.

Thus, highly favorable linear data were obtained within an L-phenylalanine concentration range of from 0 to 2 mM.

Figure 6:
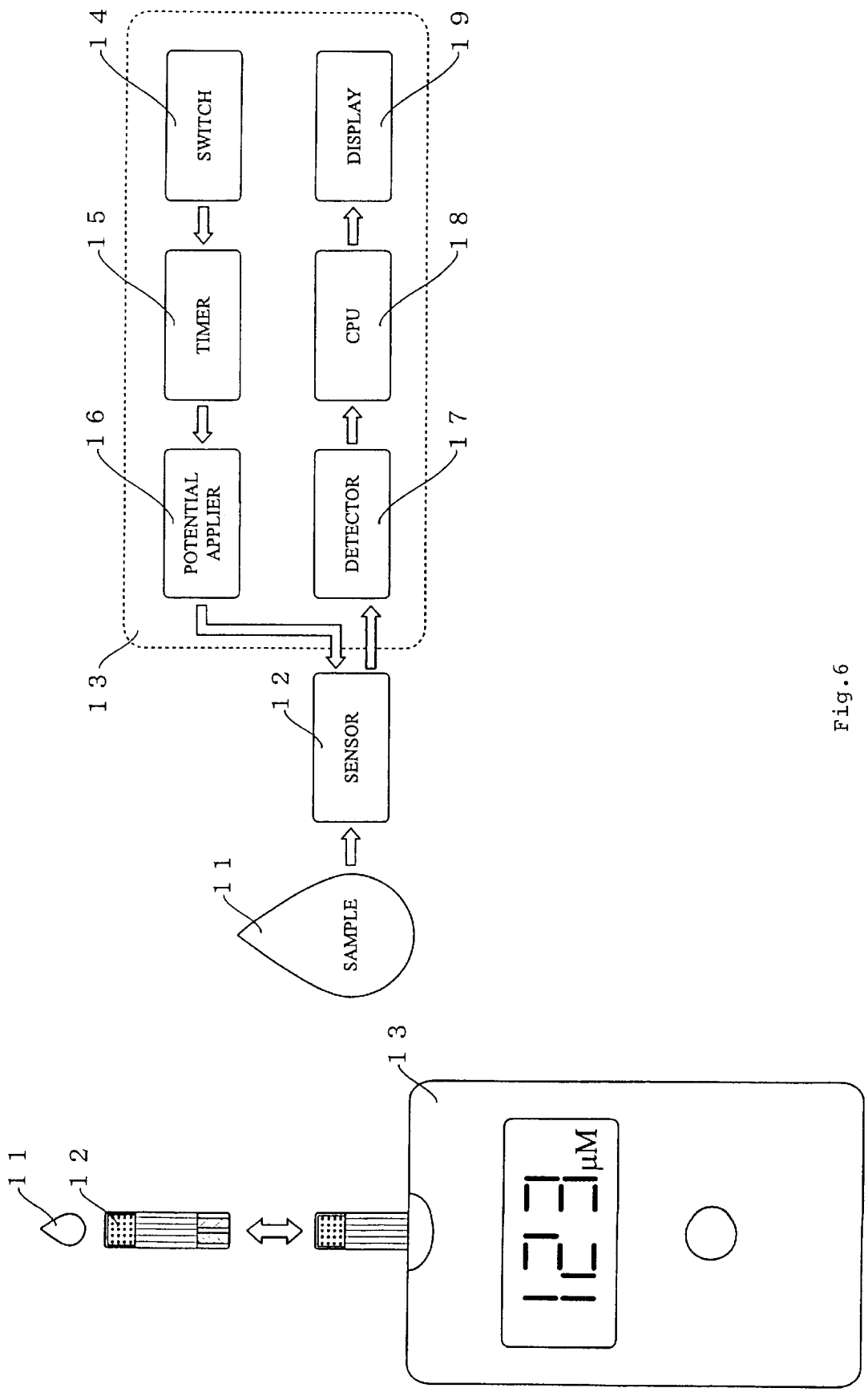
FIG. 6 is a diagrammatic illustration showing the composition of an embodiment of the portable L-phenylalanine sensor according to the present invention.

Example 5
Fabrication of Portable L-phenylalanine Sensor FIG. 6 is a diagrammatic illustration showing an L-phenylalanine sensor 12 designed by taking L-phenylalanine monitoring during daily life into consideration and a portable meter 13 for simplified determination. Now, the determination procedure will be described.

The L-phenylalanine sensor 12 is put in the portable meter 13 for the L-phenylalanine sensor. After adding a sample 11, a switch 14 is turned on to thereby initiate the determination of L-phenylalanine. After the enzyme reaction proceeds for a certain period of time controlled by a timer 15, a definite potential is applied to the sensor by a potential applier 16. The response current level thus formed in the sensor is transformed by various methods (current-potential transformation, analog-digital transformation, etc.) by a detector 17. Next, the response current level is computed into the L-phenylalanine concentration by CPU and the result is output into a display 19.

Figure 7:
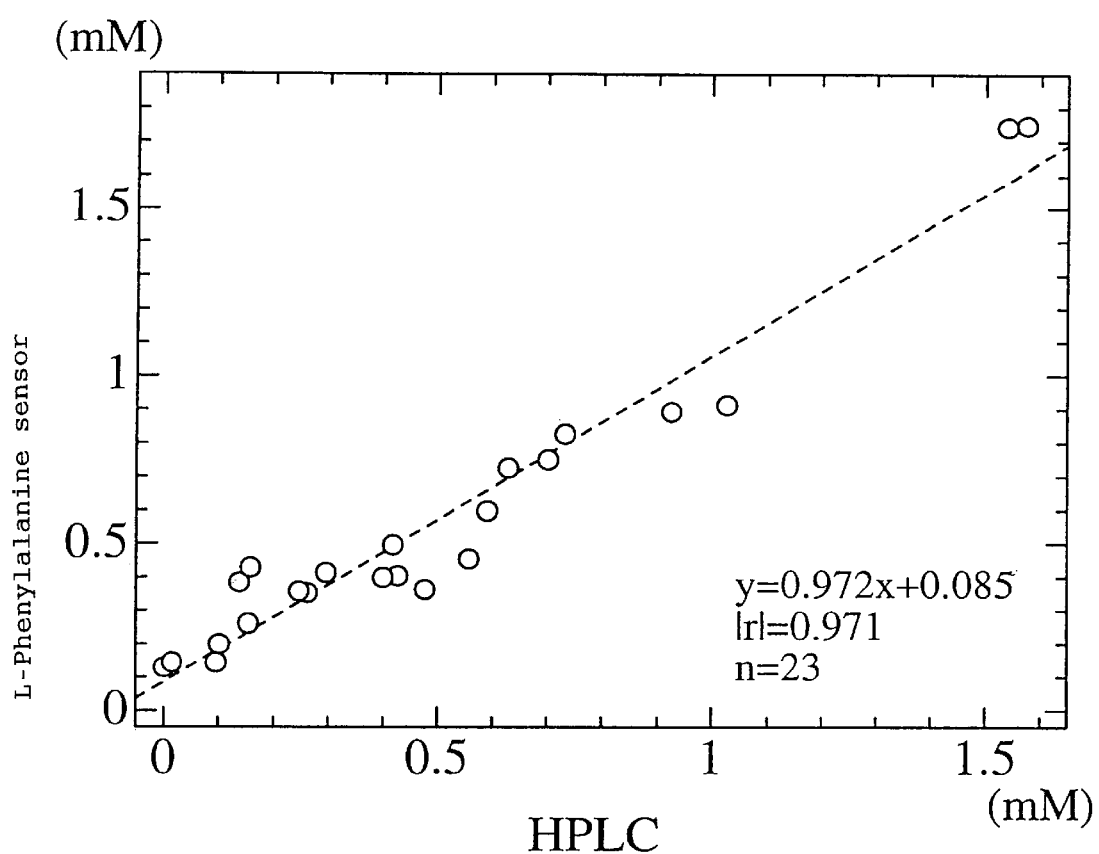
FIG. 7 is a graph which shows the correlationship between the L-phenylalanine concentrations determined by the portable L-phenylalanine sensor of Example 6 and the L-phenylalanine concentrations determined by high-performance liquid chromatography (HPLC).

Example 6
Correlationship Between L-phenylalanine Concentrations Determined by Portable L-phenylalanine Sensor and L-phenylalanine Concentrations Determined by HPLC Regarding samples containing L-phenylalanine, the correlationship was examined by using the portable L-phenylalanine sensor fabricated in the above Example 5 and HPLC. FIG. 7 shows the results.

In case of HPLC (manufactured by Hitachi), samples were deproteinized and then subjected to the determination of the L-phenylalanine concentration in accordance with the above-described method of Hayashi et al. (Journal of Chromatography, Vol. 274, p. 318 (1983)). In case of the portable L-phenylalanine sensor, the same blood samples were subjected to the determination without deproteinization.

Thus, a highly favorable correlationship (coefficient of correlation: 0.971) was observed within an L-phenylalanine concentration range of from 0 to 1.5 mM.

Figure 8:
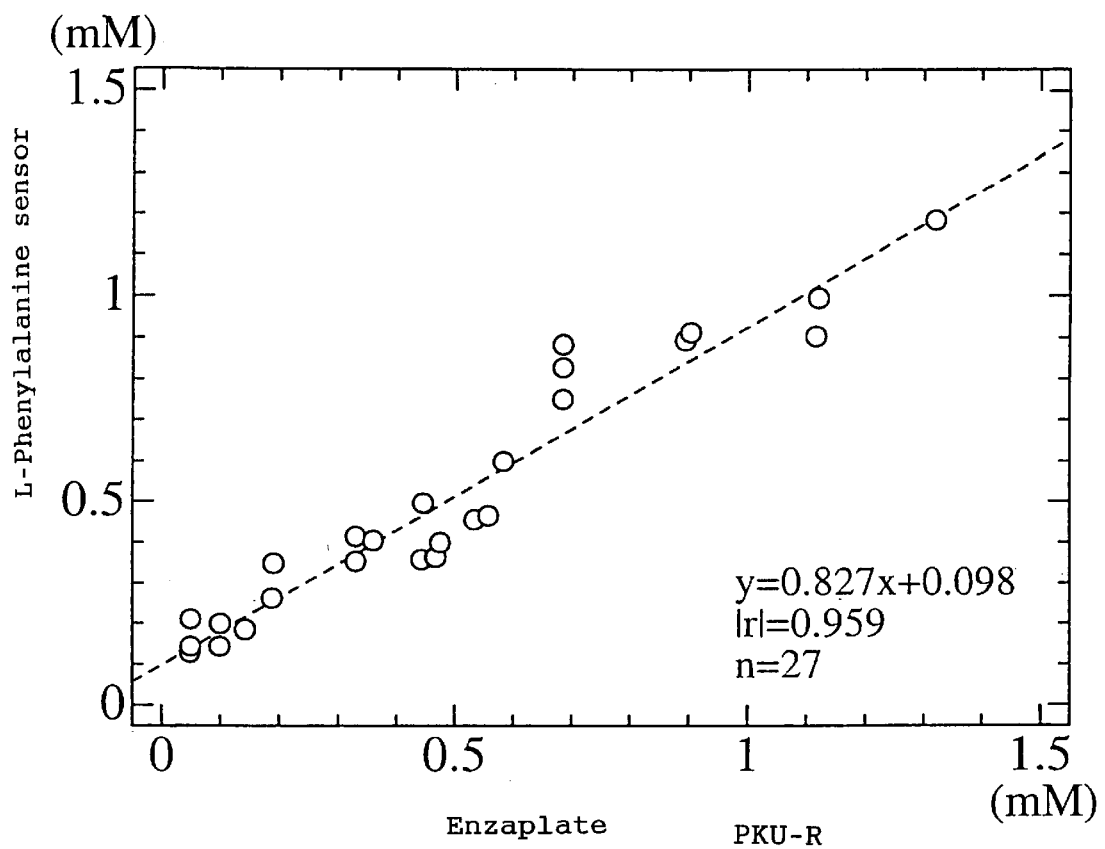
FIG. 8 is a graph which shows the correlationship between the L-phenylalanine concentrations determined by the portable L-phenylalanine sensor of Example 7 and the L-phenylalanine concentrations determined by using a clinical chemical amino acid quantification kit of the enzyme method type.

Example 7
Correlationship Between L-phenylalanine concentrations determined by portable L-phenylalanine sensor and L-phenylalanine concentrations determined by clinical chemical amino acid quantification kit of the enzyme method type As in the above Example 6, blood samples containing L-phenylalanine were subjected to the determination by using the portable L-phenylalanine sensor fabricated in Example 5 and an amino acid quantification kit to thereby examine the correlationship. FIG. 8 shows the results.

In case of the clinical chemical amino acid quantification kit (Enzaplate PKU-R manufactured by Tomakomai Clinical Laboratory), fluorescent intensities (Fluororite 1000 manufactured by Dynatec Laboratories) corresponding to L-phenylalanine concentrations were determined in accordance with the manufacturer's instruction.

Thus, a highly favorable correlationship (coefficient of correlation: 0.959) was observed within an L-phenylalanine concentration range of from 0 to 1.5 mM.

Although use was made of a two-electrode system comprising a working electrode and a counter electrode exclusively, determination can be carried out with increased accuracy by using a three-electrode system involving a reference electrode.

As discussed above, the present invention makes it possible to conveniently fabricate an L-phenylalanine sensor, wherein reaction reagents such as an enzyme and an electrode are integrated together, by using the printing method. Thus, L-phenylalanine contained in a sample can be highly accurately and conveniently quantitated electrochemically within a short period of time merely by adding a trace amount of the sample, without resort to any special measuring devices or instruments, techniques or troublesome pretreatments.

By using the L-phenylalanine sensor and a portable meter for this sensor, moreover, various measuring conditions can be eased and thus quantification can be conveniently carried out without time or place restrictions.

What is claimed is:

1. A method of determining L-phenylalanine comprising:
   (1) adding a sample to an L-phenylalanine sensor composed of an electrode system which is formed by printing with the use of a conductive material and which comprises at least a working electrode made of a material mainly comprising carbon and a counter electrode formed on an insulating support, and a reagent reaction layer which is provided in a space of said electrode system comprising a working electrode and a counter electrode formed opposite to each other, and the reagent reaction layer contains as reagents at least L-phenylalanine dehydrogenase, $NAD^+$ an or $NADP^+$ as a coenzyme and phenazine as an electron mediator and which is fixed within said electrode system, and
   (2) electrochemically quantifying L-phenylalanine.

2. An L-phenylalanine sensor having a structure composed of an electrode system which is formed by printing with the use of a conductive material and which comprises at least a working electrode made of a material mainly comprising carbon and a counter electrode formed on an insulating support, and a reagent reaction layer which is provided in a space of said electrode system comprising a working electrode and a counter electrode formed opposite to each other, and the reagent reaction layer contains as reagents at least L-phenylalanine dehydrogenase, $NAD^+$ or $NADP^+$ as a coenzyme and phenazine as an electron mediator and which is fixed within said electrode system.

3. An L-phenylalanine sensor as claimed in claim 2, wherein the reagent reaction layer comprises a hydrophilic absorbent carrier, and, in the electrode system comprising at least a working electrode and a counter electrode formed opposite to each other on an insulating support, said absorbent carrier is located in a part where an electrode reaction between these electrodes occurs and is partly protected from contact with the outside, said electrode system has a structure serving as at least a protective layer for said absorbent carrier, and said absorbent carrier providing a reaction layer for both of an enzyme reaction between a sample and the reaction reagents and the electrode reaction between an electron mediator and an electrode surface.

* * * * *